United States Patent [19]

Asahina et al.

[11] Patent Number: 5,357,550
[45] Date of Patent: Oct. 18, 1994

[54] APPARATUS FOR DIAGNOSING VASCULAR SYSTEMS IN ORGANISM

[75] Inventors: Hiroshi Asahina, Nishinasuno; Masayuki Nishiki, Otawara, both of Japan

[73] Assignee: Kabushiki Kaisha Toshiba, Kawasaki, Japan

[21] Appl. No.: 942,272

[22] Filed: Sep. 9, 1992

[30] Foreign Application Priority Data

Sep. 9, 1991 [JP] Japan .................................. 3-228971

[51] Int. Cl.⁵ ............................................. H05G 1/64
[52] U.S. Cl. .................. 378/98.5; 128/653.1; 378/98.2
[58] Field of Search .......................... 378/99; 358/111; 128/653.1

[56] References Cited

U.S. PATENT DOCUMENTS 4,821,731  4/1989  Martinelli ........................ 128/653.1

Primary Examiner—Craig E. Church
Attorney, Agent, or Firm—Oblon, Spivak, McClelland, Maier & Neustadt

[57] ABSTRACT

An apparatus is specialized in diagnosing a vascular system in an organism. The diagnostic apparatus is preferable especially to inspection of a circulatory system such as a blood vessel. The inspection can be carried out by obtaining a longitudinal structual image of a lumen of the vascular system and a stenosis index of the lumen. In order to accomplish it, the apparatus comprises an element for fluorographing the vascular system by X-rays, an element for obtaining a plurality of fluoroscopic images based on the X-ray fluoroscopic image signals supplied, an element for ultrasonic probing which has an ultrasonic probe inserted into the vascular system with a catheter, an element for obtaining a plurality of tomographic images based on the ultrasonic tomographic image signals supplied, an element for determining structure of the vascular system based on the plurality of fluoroscopic images and the plurality of tomographic images, and an element for displaying the structure of the vascular system.

51 Claims, 15 Drawing Sheets

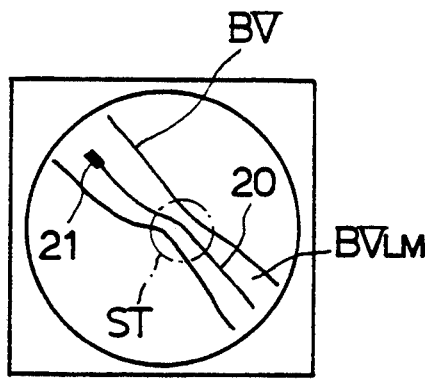
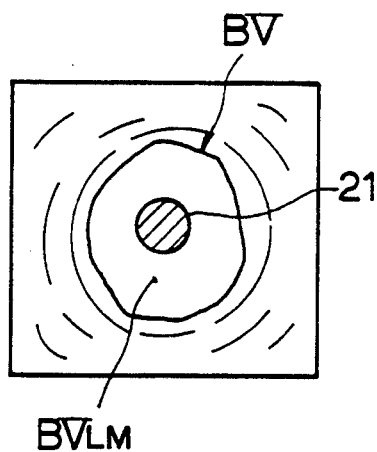
FIG. 3A  FIG. 3B
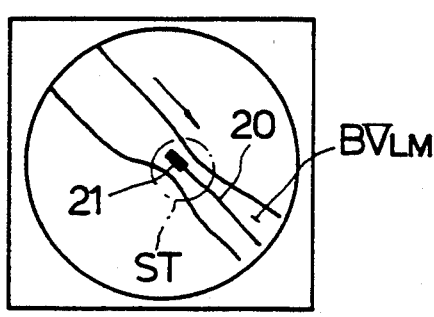
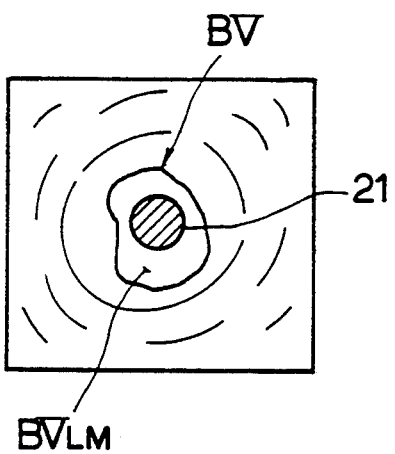
FIG. 4A  FIG. 4B
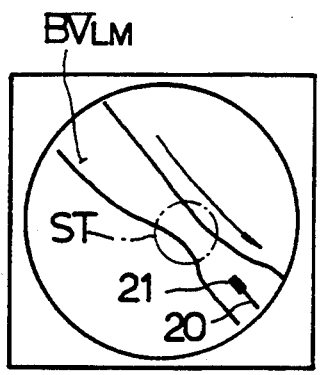
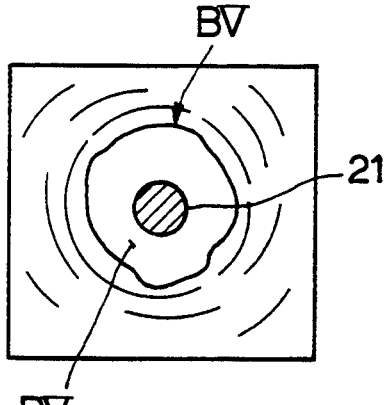
FIG. 5A  FIG. 5B

APPARATUS FOR DIAGNOSING VASCULAR SYSTEMS IN ORGANISM

BACKGROUND OF THE INVENTION

The present invention relates to an apparatus for diagnosing vascular systems, such as a circulatory system of a blood vessel, in an organism, and more particularly, to the apparatus, having a combined function by an X-ray fluoroscopic system and an ultrasonic tomographic system with a catheter, for acquiring clinical information of circulatory illness by the combined function.

In recent diagnosis of circulatory illness, angiography by X-rays diagnostic systems has been in general use for the blood vessels ranging from the head to the legs of a patient. The angiography by X-rays provides a fluoroscopic image of the blood vessels on a display device. In a typical fashion, the fluoroscopy is effective in not only qualitative diagnosis by observing it but quantitative diagnosis by measuring internal diameters of the vessel imaged. The quantitative diagnosis includes a stenosis index, the rate in internal diameter between a selected non-illness portion and a selected illness portion along the vessel being imaged, whose figure is normally shown by quick calculation on the same display with the fluoroscopic image. The stenosis index can provide important information on whether treatment of the illness is required.

However, images supplied by the X-ray fluoroscopic system remains in two-dimensionally projected images from one direction, thus being impossible to recognize the three-dimensional blood vessel accurately. For example, when calculating a cross section of the blood vessel (the value of the cross section contributes to determining the stenosis index), the value is not always accurate. In addition, obscurity in resolution exists due to an X-ray focus size and scattered rays, which decrease in most cases the accuracy of various values determined from the projected image.

On the other hand, an ultrasonic tomographic system with a catheter also provides images usable for diagnosis of circulatory illness. In the ultrasonic tomographic system with the catheter inserted into a blood vessel, the system holds an ultrasonic probe at one end portion of the catheter. The ultrasonic probe transmits ultrasonic pulse signals almost perpendicularly toward the internal wall of the blood vessel and receives their echo signals at an inserted position, so that the echo signals will be processed to image data by an image processor. The image data thus-obtained creates on a display a real-time cross-sectional tomographic image of the blood vessel, covering from its lumen to wall portion. Hence, the cross sectional tomographic image can be used for finding an illness portion such as a stenosis in the vessel.

However, the image displayed by the above ultrasonic diagnostic system is always fixed to a view in the longitudinal direction of the vessel, and thus an operator is limited to observe only a cross sectional image perpendicularly to the vessel wall at the inserted position of the ultrasonic probe. As a result, it is difficult to visualize the structure of the whole vessel in one view, even though the internal diameter of the vessel may change with its longitudinal positions because of a stenosis. The operator can transfer the catheter many times to a quantity of diagnostic positions for viewing the whole structure. However, it is impossible to view the whole structure at one time and therefore results in long diagnostic time and difficulty in operation.

SUMMARY OF THE INVENTION

Accordingly, it is a primary object of the present invention to provide a diagnostic apparatus which can supply more accurate, easy-to-recognise structure information of a vascular system such as a blood vessel in a living body.

It is another object of the present invention to provide a diagnostic apparatus preferable especially to inspection of a blood vessel.

It is still another object to provide, with relatively simple processing, a structural image extended in a longitudinal direction of the blood vessel and a stenosis index of the blood vessel.

It is still another object to provide a diagnostic apparatus which can overcome influence due to the contraction and expansion of one's heart.

It is still another object of the present invention to measure readily an absolute area and a diameter of a lumen of the blood vessel.

It is still another object of the present invention to be able to observe freely a tomographic image of the vascular system even after inspection.

These and other objects can be achieved according to the present invention, in one aspect by providing, an apparatus for diagnosing vascular systems in an organism which comprises an element for fluorographing the vascular system to be diagnosed by X-rays, the X-rays being converted to electrical image signals after having been transmitted through the organism, an element for obtaining a plurality of fluoroscopic images based on the image signals supplied by the X-ray radiographing element, an element for ultrasonic probing which has an ultrasonic probe inserted into the vascular system with a catheter, the ultrasonic probe being able to obtain ultrasonic echos representing ultrasonic tomography images of the vascular system and the ultrasonic echos being converted to electrical image signals, an element for obtaining a plurality of tomographic images based on the image signals supplied by the ultrasonic probing element, an element for determining the structure of the vascular system based on the plurality of fluoroscopic images and the plurality of tomographic images, and an element for displaying the structure of the vascular system.

Preferably, the ultrasonic probe is to be transferred through the vascular system and imaging both in the fluoroscopic image obtaining element and in the tomographic image obtaining element is carried out every predetermined sample period of time. It is also preferred that the structure of the vascular system is represented by a structural image showing longitudinal positions of the lumen and cross sectional areas of the lumen at the positions. It is also preferred that the structure is explained by stenosis indexes. Preferably, the vascular system is a blood vessel.

As a result, the combined diagnostic function derived from X-ray fluoroscopic images and ultrasonic tomographic images can provide accurate, easy-to-recognise structure information of the blood vessel in one's living body.

BRIEF DESCRIPTION OF THE DRAWINGS

The accompanying drawings which are incorporated in and constitute a part of this specification, illustrate embodiments of the invention and, together with the description, serve to explain the principles of the invention. In the drawings:

FIGS. 3A, 4A and 5A each show examples of fluoroscopic images;

FIGS. 3B, 4B and 5B show examples of tomographic images;

DESCRIPTION OF THE PREFERRED EMBODIMENTS

A first embodiment of the present invention will now be described with reference to FIGS. 1 to 12.

Figure 1:
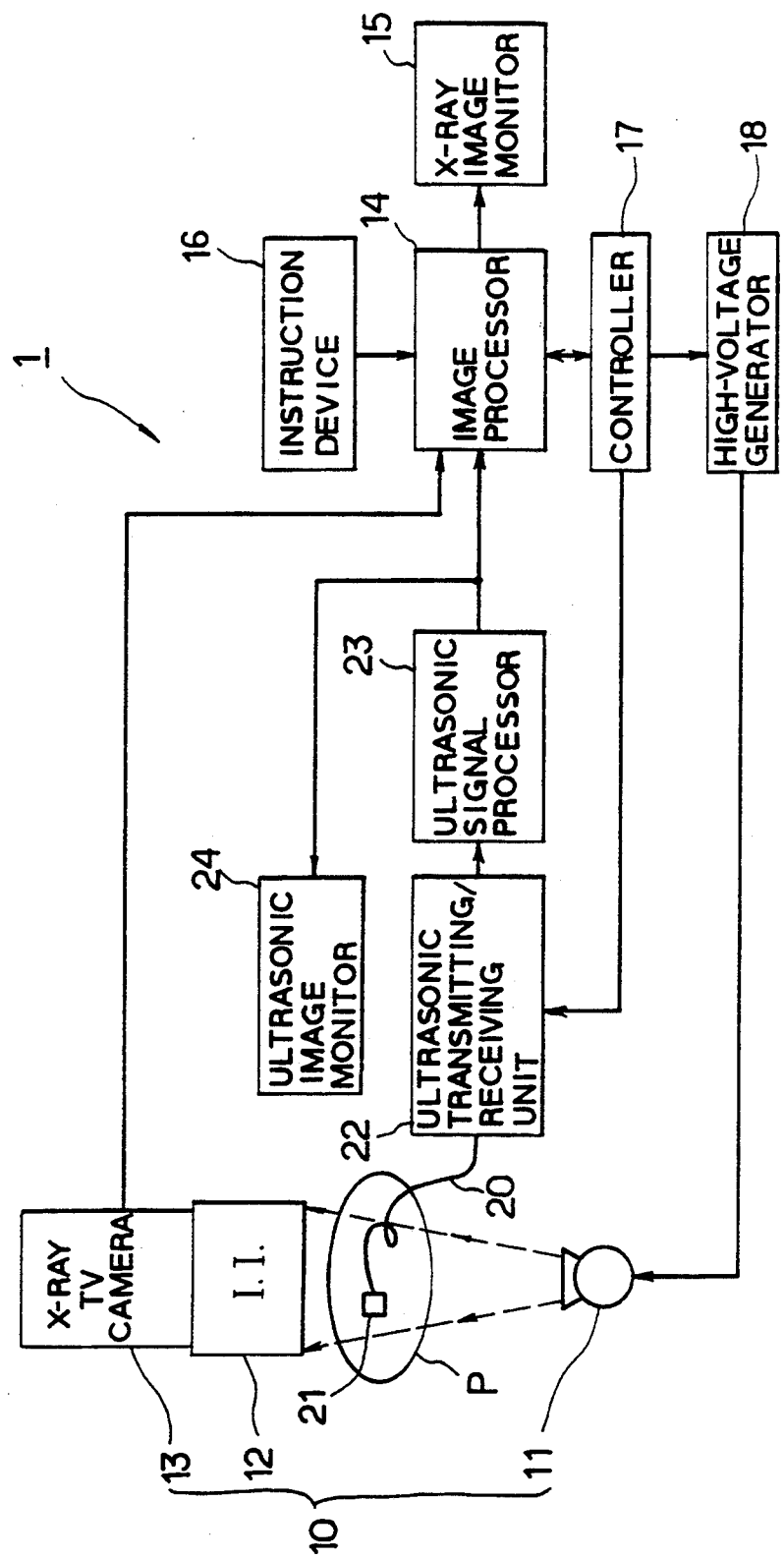
FIG. 1 represents in block form a diagnostic apparatus according to a first embodiment of the present invention.

An apparatus 1 for diagnosing vascular systems in a living body is shown in block form in FIG. 1. The diagnostic apparatus I has an X-ray fluoroscopic unit 10 comprising an X-ray tube 11, an image intensifier 12, and an X-ray TV camera 13. The X-ray tube 11 is to irradiate X-rays toward a patient P. The X-rays penetrating the patient P reach the image intensifier 12, then being converted to optical images therein. The optical images thus-converted are transmitted to the X-ray TV camera 12 to be converted again to electrical image signals.

The image signals generated by the camera 13 are transmitted to an image processor 14, which makes up part of the diagnostic apparatus 1, including a computer system therein. The image processor 14 is in charge of image processing including noise correction and gradation correction. The processed image signals are then supplied to an X-ray image monitor 15, which also makes up part of the diagnostic apparatus 1, and displayed on the monitor 15 as an X-ray fluoroscopic image of the patient P.

The image processor 14 is coupled to an instruction device 16 by which an operator is able to have it start image recording.

There is also provided a controller 17 having a computer system therein. The controller 17 is in charge of controlling time of the whole apparatus 1, in addition to control including process timing in the image processor 14.

The above-mentioned X-ray tube 11 is coupled to a high-voltage generator 18 being able to supply high voltage for X-ray irradiation to the X-ray tube 11 under control of the controller 17.

In an ordinary fashion of X-ray fluoroscopy, continuous X-rays are used. Further, in order to reduce obscurity due to moving object in fluoroscopic images, pulsed X-rays may be used. In such a case, the high-voltage generator 18 will provide the X-ray tube 11 pulsed high-voltage signals synchronized with image signals, in response to control from the controller 17.

Now, an ultrasonic diagnosing system incorporated in the above diagnostic apparatus 1 will be described.

In the ultrasonic diagnosing system, as shown in FIG. 1, there is provided a catheter 20 inserted into an aimed blood vessel of the patient P. An ultrasonic probe 21 is rotatably placed in one end portion of the catheter 20 and electrically connected through the catheter 20 to an ultrasonic transmitting/receiving unit 22 which operates under control of the controller 17. Thus, when the ultrasonic transmitting/receiving unit 22 starts its operation in mechanical rotating scan mode, for example, the ultrasonic probe 21 is able to radiate ultrasonic pulses perpendicularly toward the vessel wall and to receive their echo pulses at an inserted position.

The ultrasonic echo pulses thus-supplied are then sent to a signal processor 23 to be constructed into image data diagnosed. The constructed image data are then sent to not only an ultrasonic image monitor 24 for displaying therein but the above-described image processor 14. In this case, the cross-sectional image of the ultrasonic probe 21 itself is also delineated on the screen of the ultrasonic image monitor 24.

Figure 2:
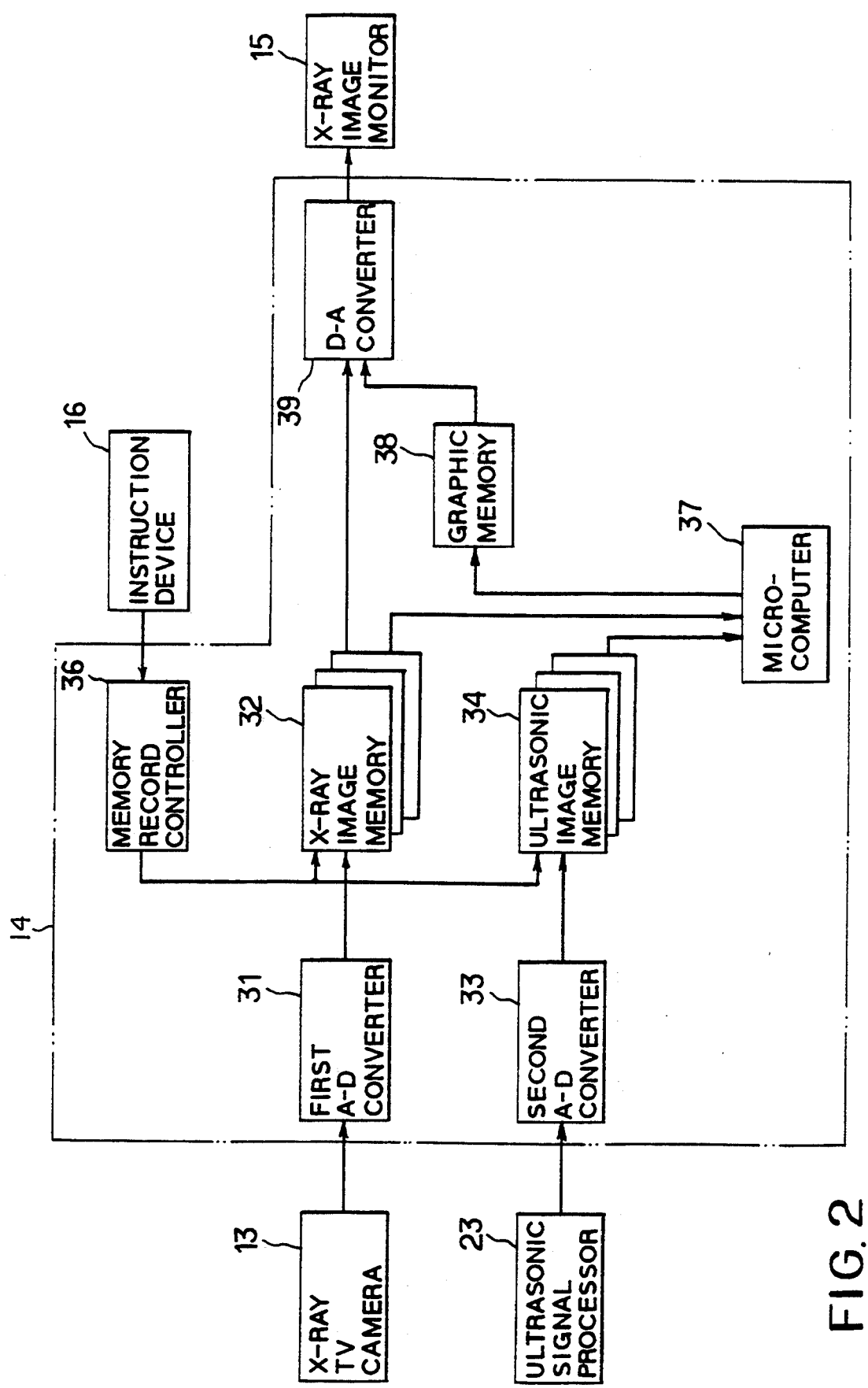
FIG. 2 represents in block form an image processor in the diagnostic apparatus in the first embodiment.

FIG. 2 represents in detail the above-explained image processor 14. As shown in the figure, the image processor 14 comprises a first analog to digital (A-D) converter 31 at its input side, which receives the image signals outputted from the X-ray TV camera 13. The image signals converted to digital words by the A-D converter 31 will be sent to an X-ray image memory 32 to be stored therein. The X-ray image memory 32 comprises a plurality of frame memories.

The image processor 14 also comprises a second A-D converter 33 at its input side, which receives the image signals outputted from the signal processor 23 in the ultrasonic diagnostic system. The image signals converted to digital words by the A-D converter 33 will then be sent to an ultrasonic image memory 34 to be stored therein. The ultrasonic image memory 34 comprises a plurality of frame memories.

In the image processor 14, there is also provided a memory record controller 36 connected to the instruction device 16, for which an operator can request a start of image recording. In response to an instruction from the instruction device 16, the memory record controller 36 sends both of the image memories 32 and 34 a command to make them start storing image at every certain period of time. As a result, X-ray fluoroscopic images and ultrasonic images can synchronously be stored into the frame memories of the X-ray image memory 32 and the ultrasonic image memory 34, respectively, at every certain period of time.

The image data thus-stored in the image memories 32 and 34 are read out frame by frame by a microcomputer 37 installed therein as one of the essential parts of the image processor 14.

The microcomputer 37 is designed to carry out processing of determining dimensions relating to structure of a diagnosed blood vessel and its stenosis index. In order to perform the processing, as preparatory steps, the microcomputer 37 also carries out calculation for determining the inserted position of the ultrasonic probe 21 based on the X-ray fluoroscopic image data and the cross-sectional area of the lumen of the diagnosed blood vessel based on the ultrasonic image data. The thus-determined image data relating to the blood vessel structure and its stenosis index are sent to a graphic memory 38 for composing a picture therein.

The image data stored in the graphic memory 38 are then outputted to a digital-to-analog(D-A) converter 39, placed at the output side of the image processor 14, which also receives the fluoroscopic image data supplied from the X-ray image memory 32. The analog image signals converted by the D-A converter 39 will then be sent to the above-explained X-ray image monitor 15, and be displayed thereon as images representing the vessel structure and the stenosis index, together with the X-ray fluoroscopic image previously described. It should be noted that the projected image of the ultrasonic probe 21 be displayed in a fluoroscopic image of tissues on the same screen of the X-ray image monitor 15.

As one of modified embodiments, the blood vessel structure and the stenosis index can be displayed on the ultrasonic image monitor 24 instead of the X-ray image monitor 15.

Now, with reference to FIGS. 3 to 11, the manner by which to diagnose a blood vessel will be explained.

In FIGS. 3A to 5B, reference BV and $BV_{LM}$ each represent a blood vessel being diagnosed and the lumen(filled with blood) of the blood vessel BV. ST represents a stenosis as an illness portion. Each combination of FIGS. 3A and 3B, 4A and 4B, and 5A and 5B makes a pair of images according to X-ray radiography and ultrasonic imaging at the same diagnostic time, that is, at the same inserted position of the ultrasonic probe 21.

First, under the activation of the diagnostic apparatus, an operator is to insert the catheter 20 into a blood vessel BV to be diagnosed and guide it to a stenosis ST in the blood vessel BV, as shown in FIGS. 3A and 3B, confirming the inserted position of the ultrasonic probe 21 in the X-ray fluoroscopic image displayed on the X-ray image monitor 15. At this stage, it is desirable for the catheter 20 to be carried over the stenosis ST and to a position which is very small distance ahead of it. Carrying the catheter 20 in this fashion enables the probe 21 to stay at a non-illness portion in the vessel BV as an initial diagnostic position. The lumen $BV_{LM}$ at the initial position is wider in area than that of the stenosis ST.

Then, the operator is to request the instruction device 16 so as to begin storing images in the image processor 14. This instruction permits both of the image memories 32 and 34 to store repeatedly image data supplied by the X-ray fluoroscopic unit 10 and the ultrasonic signal processor, respectively, as explained above.

After the initiation of the image aquisition, the catheter 20 will be pulled back at an appropriate speed by hand through the blood vessel BV. The pulling of the catheter 20 (i.e., the ultrasonic probe 21) will cause the probe 21 to be transferred through the stenosis ST as shown in FIGS. 4A and 4B, and then to reach a second non-illness portion as shown in FIGS. 5A and 5B. On the way from the start to end of this transfer operation, a large number of frames of images are acquired every repetition interval of time in respect to both the X-ray fluoroscopic and ultrasonic tomographic images by the above-described fashion.

Figure 6:
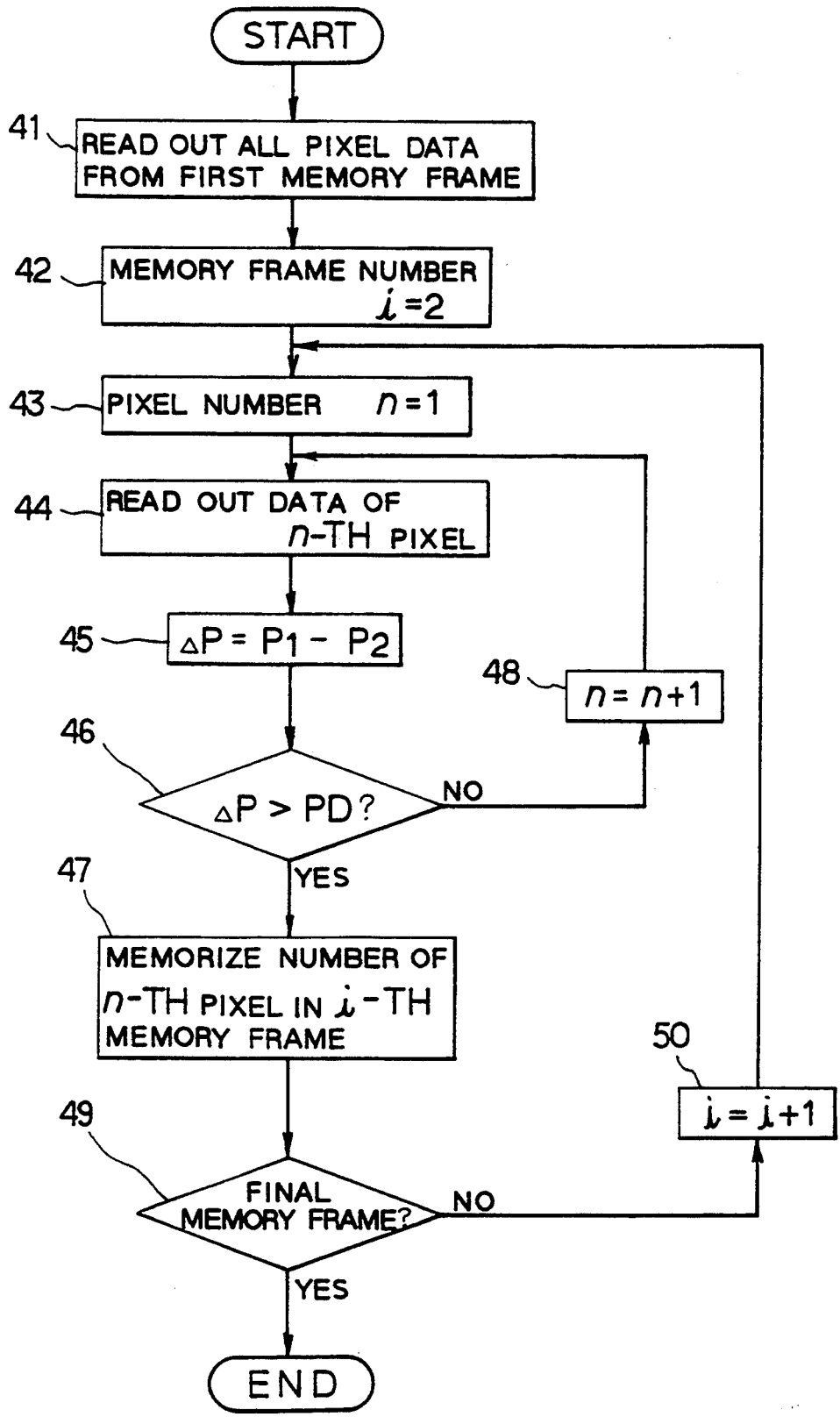
FIG. 6 is a flowchart showing processing for fluoroscopic images.

FIG. 6 is a flowchart representing a series of procedures, carrried out by a CPU of the microcomputer 37 placed in the image processor 14, for determining positions of the ultrasonic probe 21 based on a large number of X-ray fluoroscopic image data stored in the X-ray image memory 32.

Figure 7:
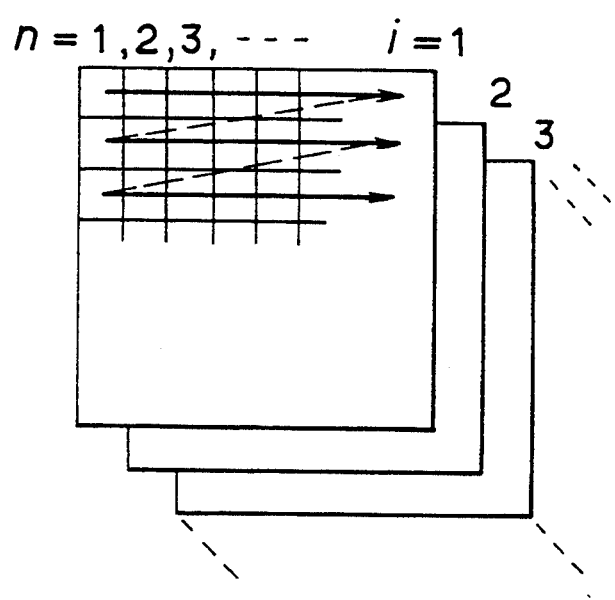
FIG. 7 depicts a direction in reading out fluoroscopic data from frame memories.

In this embodiment, the pixel number n (n=1, 2, 3, . . .) of each frame memory i (i=1, 2, 3, . . . ) in the memory 32 is put as shown in FIG. 7. That is, the pixel number n starts from a pixel (n=1) positioned uppermost and leftmost toward its right-hand side transversely (n=2, 3, . . . , N) in the first row. In the second row, the pixel number n also starts from a leftmost pixel (n=N+1) toward its right-hand side transversely to a rightmost pixel (n=2N). In the same way, this numbering continues up to the lowermost row.

At Step 41 in FIG. 6, the CPU of the microcomputer 37 reads out, in order of the pixel numbers, all the image data stored in the pixels of the first frame memory i (=1), the data of which had been collected on condition that the ultrasonic probe 21 was stopped at the non-illness initial diagnostic position.

Then at Step 42, the CPU designates the frame number i as i=2. Then procedures of Steps 43 to 46 will be carried out by the CPU for determining the transferred position of the probe 21.

Namely, the pixel number n=1 is designated at Step 43 and the image data of the n-th(n=1) pixel is read out at Step 44. Further, at Step 45, for judgement if the probe 21 is transferred, subtraction "P1−P2" will be performed, where P1 is a pixel intensity of the n-th pixel read out at Step 41 and P2 is a pixel intensity of the n-th pixel read out at Step 44. Here, the pixel intensity corresponds to X-ray transmission through the patient P. And at Step 46, the result $\Delta P$ (=P1−P2) will be compared with a predetermined threshold level PD for noise cancellation. The threshold level is designed to be a positive value expressing X-ray noise level averagely contained in X-ray fluoroscopic images. Thus, the comparison here determines whether $\Delta P > PD$ is true or not. If $\Delta P > PD$ is true, the ultrasonic probe 21 has been transferred to the n-th pixel in i-th frame memory. Then the number of the n-th pixel is memorized at Step 47.

On the other hand, when the result $\Delta P$ at step 45 becomes $\Delta P \leq PD$, it is known that the n-th pixel in the i-th frame memory now examined has no information relating to the transfer of the probe 21. That is, the ultrasonic probe 21 does not exist at a position corresponding to the n-th pixel in the i-th frame memory. In this case, therefore, processing will proceed to Step 48, wherein the pixel number n will be increased to n=n+1. After this increase of the number n, the processing according to Steps 44 to 46 will be repeated until the transferred position (i.e., pixel number) of the probe 21 is determined.

After completing the memorization of the pixel number at Step 47, the procedure at Step 49 will then be done, whereat the CPU judges that the examination for tracing the probe 21 has been done for all frame memories in the X-ray image memory 32. When non-examined frame memories still exist, the CPU will make its processing go on to Step 50 to let i=i+1. Thus, the processing in Steps 43 to 49 is repeated for tracing the probe 21 until completing examination of the final frame memory. If the answer is YES at Step 49, the processing will end.

It is also to be noted that the initial position of the ultrasonic probe 21, that is, the position of the ultrasonic probe 21 in the first frame is determined by designating pixels which produce negative values in subtracting the pixel intensities of the second frame memory from those of the first frame memory.

Figure 8:
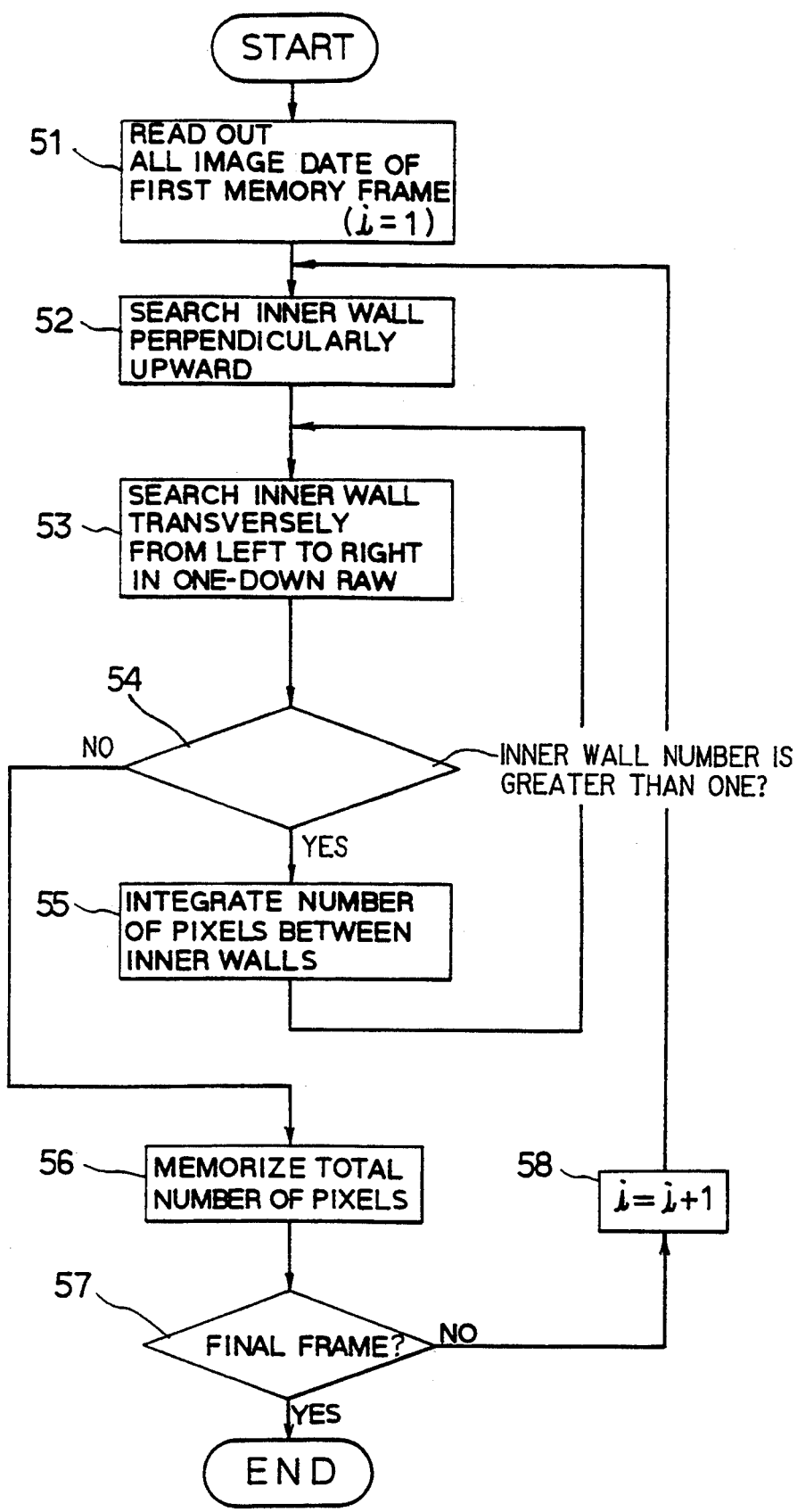
FIG. 8 is a flowchart showing processing for tomographic images.
Figure 9:
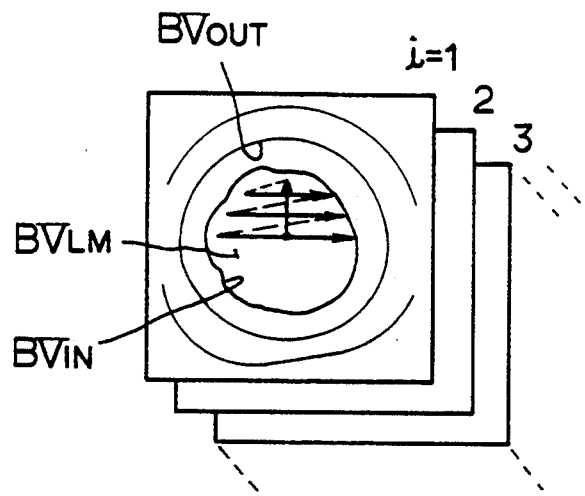
FIG. 9 depicts a direction in reading out tomographic data from frame memories.

FIG. 8 is a flowchart showing a series of procedures, carried out also by the CPU of the microcomputer 37, for determining the pixel number corresponding to the lumen $BV_{LM}$ of the blood vessel BV based on the image data stored in the ultrasonic memory 33. The stored image data are constructed as shown in FIG. 9, in which reference $BV_{IN}$ and $BV_{OUT}$ represent the inner wall and outer wall of the blood vessel BV.

At Step 51 in FIG. 8, all image data stored in the first frame memory of the memory 34 (frame number i=1) are read out. At Step 52, in the first image plane according to the first frame memory, the pixel equal in pixel intensity to the inner wall $BV_{IN}$ is searched with the CPU examining pixels corresponding to the lumen $BV_{LM}$. In this case, an examining direction is fixed (see arrows shown in FIG. 9); first the pixel at the image center is examined and then pixels going upward and perpendicularly are examined one after another. There is a large amount of difference in pixel intensity between the lumen $BV_{LM}$ and the inner wall $BV_{IN}$, thus the difference permitting the above search.

After having found the inner wall $BV_{IN}$ in the upward direction, at Step 53, the CPU brings its search point down to the one-step lowered row, and the CPU begin the above search from the leftmost pixel (this pixel does not always correspond to the lumen) transversely to the rightmost pixel in the lowered row.

Then at Step 54, it is judged whether the number of the pixel point of the inner wall searched at Step 53 is greater than one. When being judged that the number is one, it means that the lumen $BV_{LM}$ could not be found in the assigned row. To the contrary, when being judged that the searched number is more than one, it means that the lumen $BV_{LM}$ has been found there.

Thus, if judgement YES is concluded at Step 54, the CPU counts the total number of pixels existing along the assigned row in the lumen at Step 55, the distance of the lumen in the assigned row being limited to a distance determined by both end pixel points of the inner walls $BV_{IN}$ in the assigned row.

Then, the above-explained procedures at Steps 53 to 55 are repeated, counting the total number of pixels in each row gradually lowered. In the repetition, the repeatedly assigned row has finally come to the bottom of the lumen $BV_{LM}$, the CPU judges YES at Step 54, because the pixel number the inner wall $BV_{IN}$ is counted to be "one".

The judgement NO at Step 54 makes the processing proceed to Step 56. At Step 56, the total number of pixels corresponding to the area of the lumen $BV_{LM}$ are counted and memorized based on the counted pixel numbers for each row at Step 55.

Then at Step 57, the CPU judges that the above integration in respect to the final frame memory of the ultrasonic image memory 34 has already finished. When another frame memory still remains, the procedure at Step 58 will be carried out, and the frame number will being went forward by i=i+1. As a result, the procedures from Steps 53 to 59 are repeated in the same fashion described. When the final frame memory is concluded at Step 57, the integration processing will end.

Further, the total number of pixels corresponding to the cross sectional area of the probe 21 is examined in the same manner as above and is memorized.

Next, structure of the blood vessel BV and its stenosis index will be determined using the pixel numbers expressing the transferred positions of the probe 21 and the integrated pixel numbers corresponding to the lumen, both of which have already been found and memorized.

First, based on the pixel number $n_i$ tracing the ultrasonic probe 21 in each frame memory of the image memory 32, transferred distances of the probe 21 from the initial position will be calculated by the CPU of the microcomputer 37.

Now assume a matrix size for each of the frame memories to be S. For each frame memory, the position of the probe 21 can be converted into a coordinate $(x_i, y_i)$ based on its pixel number $n_i$. The pixel number $n_i$ is divided by the matrix size S a quotient $y_i$ and a rest $x_i$ can be produced. The result $(x_1, y_1)$ for the first frame memory is an initial coordinate. Then using $x_i$ and $y_i$ for each frame, the transferred distance $L_i$ is calculated by $$L_i = ((x_i - x_1)^2 + (y_i - y_1)^2)^{\frac{1}{2}}.$$

Thus, the CPU determines the initial position $(x_1, y_1)$ appropriately in the graphic memory 38 and delineates the positions of the transferred distances $L_i \ldots L_i (i=2, 3, \ldots)$ in succession in the memory 38.

Second, the integrated pixel number in the first frame memory of the image memory 34 constitutes a standard lumen diameter $W_1$ (for example, $W_1 = 1$) and the standard lumen diameter $W_1$ is delineated at the initial position $(x_1, y_1)$ in the graphic memory 38.

Further, the integrated pixel number in the second frame memory is divided by that in the first frame memory to produce a ratio $W_2$. The ratio $W_2$ is then delineated at the second position determined by the transferred distance $L_2$ in the memory 38. This delineation can made such that the diameters $W_1$ and $W_2$ are parallel to each other and a center line passes perpendicularly through the diameters $W_1$ and $W_2$, as shown in FIG. 10.

Figure 10:
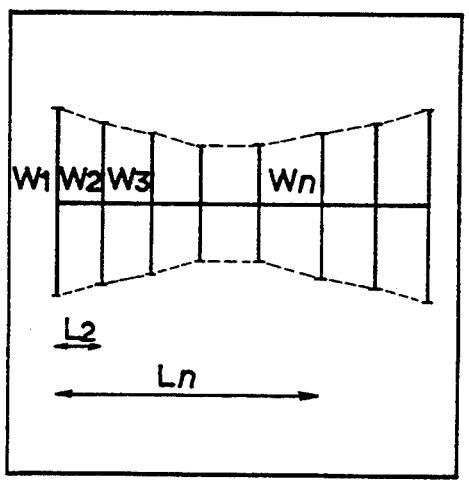
FIG. 10 is an illustration showing two-dimensionally transferred positions of an ultrasonic probe and areas of the lumen at each transferred position.

For all the frame memories, the above calculation and delineation are carried out, hence forming a structure of the diagnosed blood vessel BV as shown in FIG. 10. In FIG. 10, the cross sectional areas of the lumen at the transferred positions are expressed one-dimensionally in each longitudinal direction, but are expressed two-dimensionally in the transverse direction.

Moreover, there are provided two types of stenosis indexes, which are both relative values. One is a stenosis index representing the cross sectional area of the lumen and the other a stenosis index representing the diameter of the lumen. The stenosis index SI(area) representing the cross sectional area can be calculated by $$SI(area) = \{(MX - MN)/MX\} \times 100(\%),$$

where MX and MN are maximum and minimum values in all of the integrated pixel numbers. The stenosis index SI(diam.) representing the lumen diameter can be calculated by $$SI(diam.) = \{(MX^{\frac{1}{2}} - MN^{\frac{1}{2}})/MX^{\frac{1}{2}}\} \times 100 \ (\%)$$

Both of the indexes SI(area) and SI(diam.) are delineated in the graphic memory 38.

Figure 11:
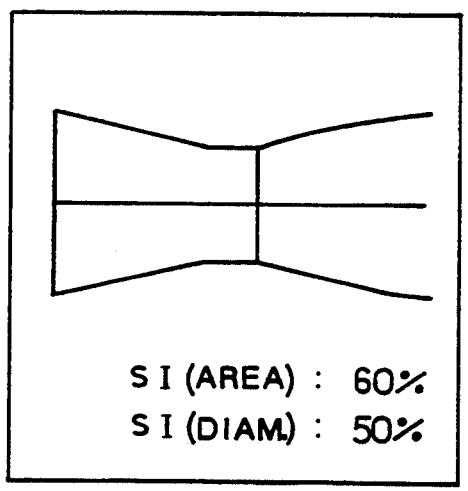
FIG. 11 shows an example of a structural image of the blood vessel.

The stored data in the graphic memory 38 is then supplied, under control of the controller 17, to the X-ray image monitor 15 by way of the D-A converter 39. As a result, the structure of the blood vessel BV is displayed with the two stenosis indexes, as shown in FIG. 11. The image of FIG. 11 can be displayed, either independently of the fluoroscopic X-ray image or superimposedly with it.

The structure image shown in FIG. 11 provides a highly concrete figure. The operator can observe easily and understandably the lumen $BV_{LM}$, especially its details at each point in the longitudinal direction of the vessel. Therefore, the apparatus here can provide more accurate information, including stenosis indexes, of the blood vessel, compared with the conventional techniques.

Figure 12:
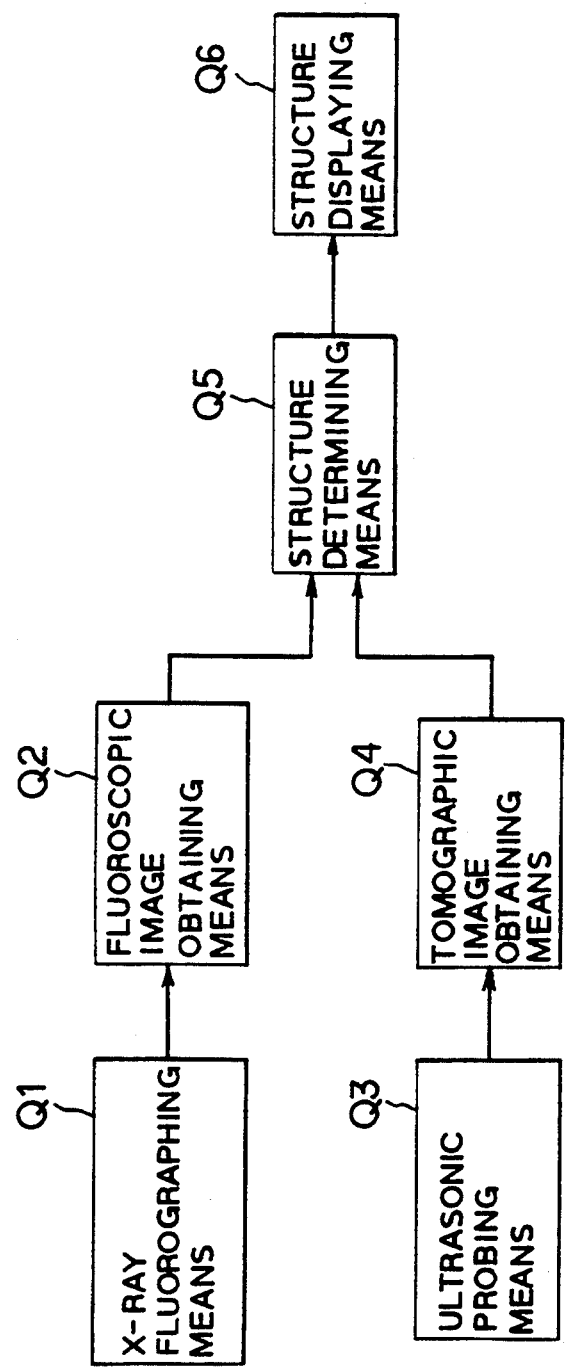
FIG. 12 shows in block form a constructional relation between the first embodiment and the present invention.

This embodiment includes the components of the present invention, as illustrated in FIG. 12. That is, the X-ray fluoroscopic unit 10 composes an X-ray fluorographing means Q1. The A-D converter 31, the X-ray image memory 32, the instruction device 16 and the memory record controller 36 compose a fluoroscopic image obtaining means Q2. Also, the ultrasonic probe 21 and the ultrasonic transmitting/receiving unit 22 make up an ultrasonic probing means Q3. The ultrasonic signal processor 23, the A-D converter 33, the ultrasonic image memory 34, the instruction device 16 and the memory record controller 36 compose a tomographic image obtaining means Q4. Still, the microcomputer 37 and the graphic memory 38 constitute a structure determining means Q5. Further, the D-A converter 39 and X-ray image monitor 15 constitute a structure displaying means Q6.

Figure 13:
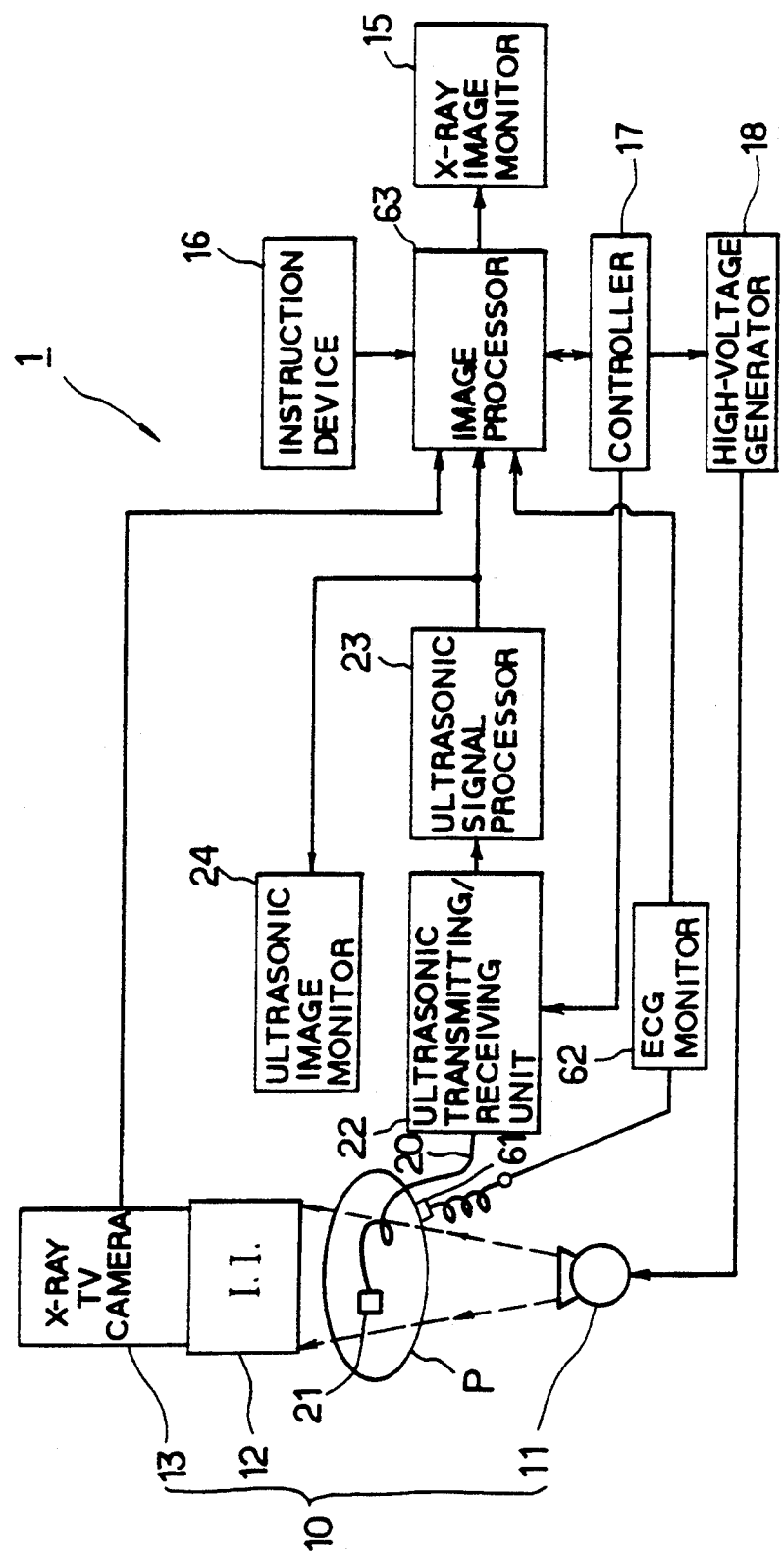
FIG. 13 represents in block form a diagnostic apparatus according to a second embodiment of the present invention.
Figure 14:
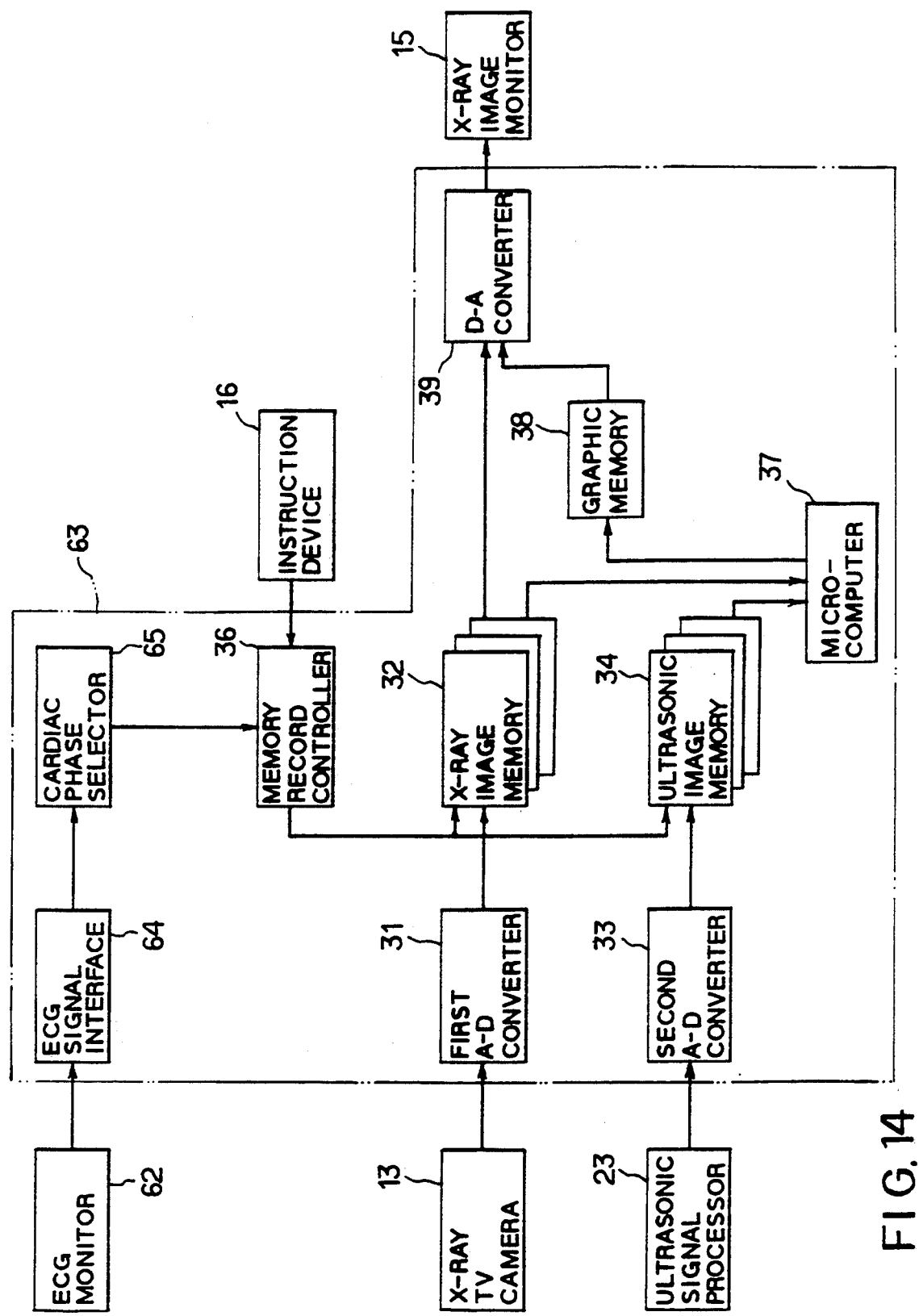
FIG. 14 represents in block form an image processor in the diagnostic apparatus in the second embodiment.

With reference to FIGS. 13 and 14, a second embodiment of the present invention will now be described. In the following embodiments, the same components as ones in the first embodiment will be cited by the same reference numerals for simplicity.

The diagnostic apparatus 1 depicted in FIG. 13 further comprises an ECG(electrocardiograph) sensor 61, attached to the patient P, to detect electric pulses due to the activity of the patient's heart. The ECG sensor 61 is electrically coupled to an ECG monitor 62 and the ECG monitor 62 is then coupled to an image processor 63. As a result, an electrical signal detected by the ECG sensor 61 is to be supplied to the ECG monitor 62, wherein the signal is converted into ECG signal. The converted signal is then outputted into the image processor 63.

The image processor 63, which also receives the signals supplied by the previously-explained X-ray TV camera 13 and ultrasonic signal processor 23, is composed as shown in FIG. 14. In the processor 63, the ECG signal from the ECG monitor 62 is received, by way of an ECG signal interface 64, by a cardiac phase selector 65. The cardiac phase selector 65 generates a timing signal having a constant interval of time, according to the inputted ECG signal. The timing signal thus-generated is supplied, as a synchronized signal for image recording, to both of the X-ray and ultrasonic image memories 32 and 34 by way of the memory record controller 36. Consequently, the data of X-ray fluoroscopic images and the data of ultrasonic tomographic images can be stored frame by frame into the image memories 32 and 34 each at a constant timing from the contraction or expansion of one's heart.

The microcomputer 37, therefore, can determine with higher accuracy the structure and stenosis rate of a blood vessel, even though the position and diameter fluctuates due to the contraction and expansion of one's heart.

In this embodiment, the ECG monitor 62 corresponds to the monitoring means of the present invention. The ECG signal interface 64 and the cardiac phase selector 65 constitute the selecting means.

Figure 15:
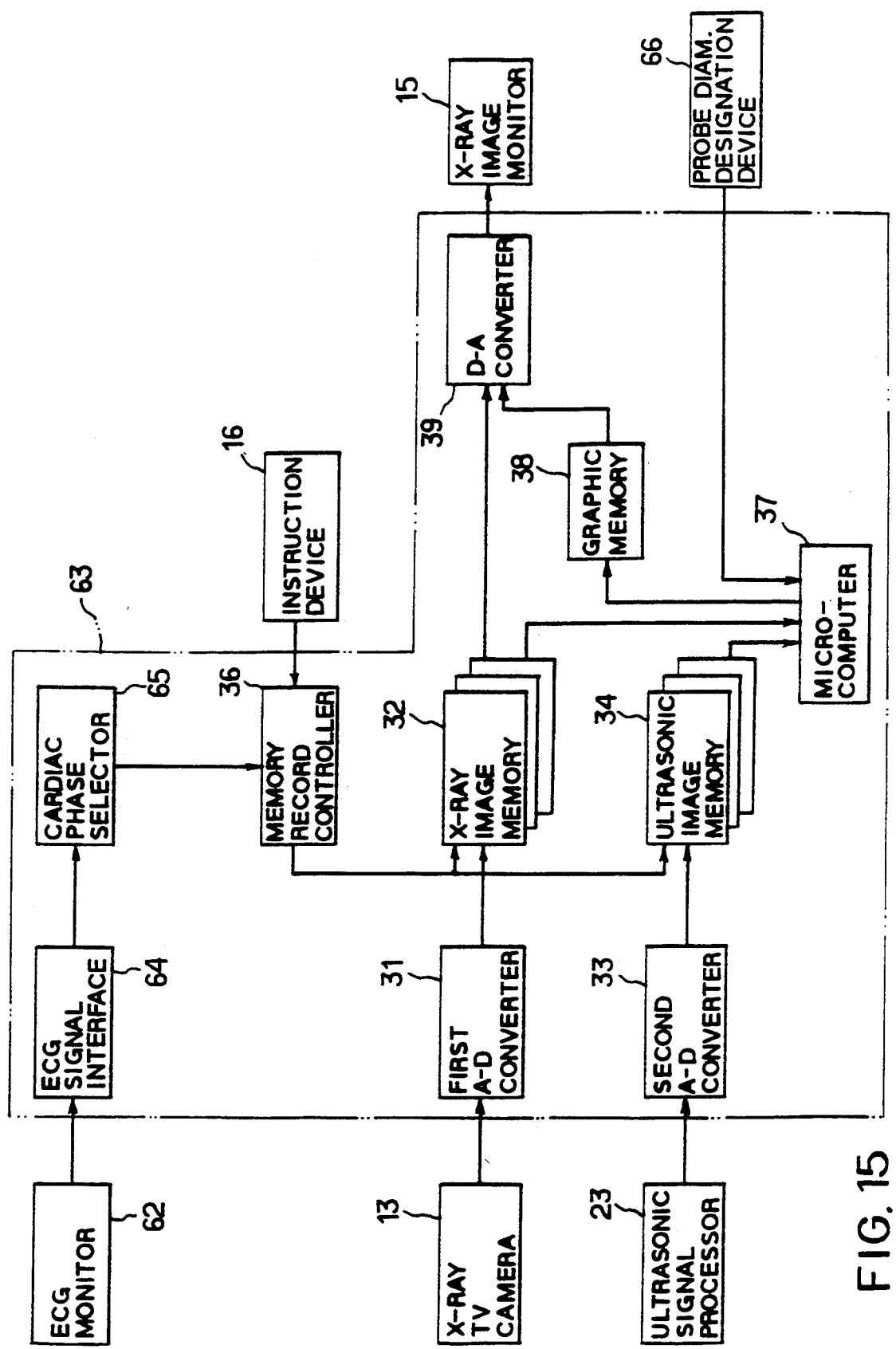
FIG. 15 represents in block form an image processor in the diagnostic apparatus in a third embodiment of the present invention.
Figure 16:
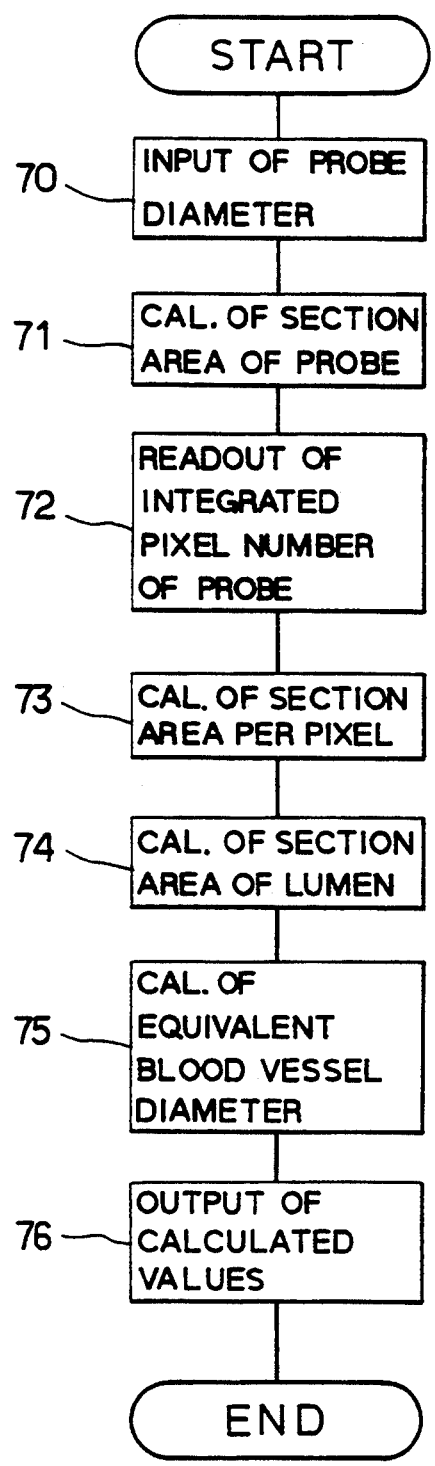
FIG. 16 is a flowchart showing calculation processing to an equivalent lumen diameter.

According to FIGS. 15 and 16, a third embodiment of the present invention will be described. In this embodiment, the apparatus 1 comprises a probe diameter designation device 66 by which an operator can designate the diameter of the ultrasonic probe 21 being used. In response to a designation signal from the designation device 66, the microcomputer 37 in the image processor 63 will carry out the procedures shown in FIG. 16. First, at STEP 70 in FIG. 16, the designation signal specifying the diameter of the probe 21 is taken in by the microcomputer 37. At STEP 71, the transverse section area of the probe 21 is calculated based on the inputted diameter. Then at STEP 72, the integrated pixel number corresponding to the section area of the probe 21 is read out. The integrated pixel number has already been calculated as described above. Thus, at next STEP 73, the microcomputer 37 calculates the section area per pixel by dividing the entire section area of the probe 21 by the integrated pixel number, and moreover, at STEP 74, it calculates the transverse section area of the lumen $BV_{LM}$ by multiplying the divided value at STEP 73 by the integrated pixel number corresponding to the area of the lumen $BV_{LM}$. In addition, at STEP 75, dividing the calculated section area at STEP 74 by the ratio of the circumference provides an equivalent blood vessel diameter, which is an absolute value. Finally, the microcomputer 37 outputs the section area of the lumen $BV_{LM}$ and the equivalent blood vessel diameter to the graphic memory 38 to display them.

The above processing thus enables the X-ray image monitor 15 to display the section area of the lumen $BV_{LM}$ and the equivalent blood vessel diameter, together with the structural image and the stenosis indexes. As a result, the combined display of the relative value (i.e., stenosis indexes) and the absolute values (lumen section area and equivalent blood vessel diameter) contributes to more accurate diagnosis.

In this embodiment, the probe diameter designation device 66 composes the designating means of the present invention. Moreover, the processing in FIG. 16 corresponds to the calculating means.

According to FIGS. 17 to 22, a fourth embodiment of the present invention will be described.

Figure 17:
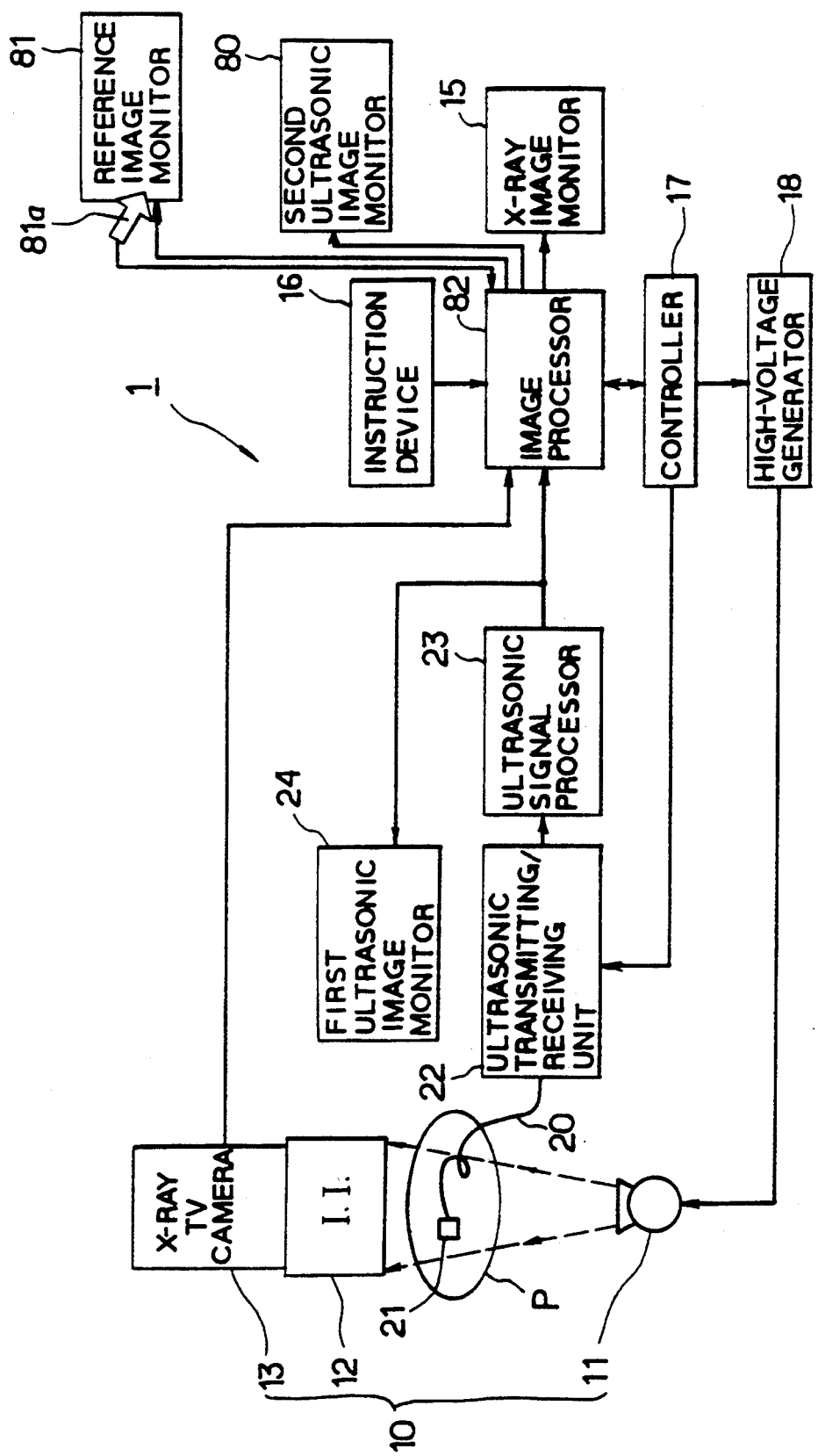
FIG. 17 represents in block form a diagnostic apparatus according to a fourth embodiment of the present invention.

As shown in FIG. 17, the apparatus 1 further comprises a second ultrasonic image monitor 80, wherein the ultrasonic image monitor 24 is referred to as a first one, and a reference image monitor 81, both are electrically connected to the image processor 82. The reference image monitor 81 has a pointing device 81a by which an operator can designate a desired position on the monitor 81. The pointing device 81a is composed of a light-pen, touch-screen, mouse or keyboard.

Figure 18:
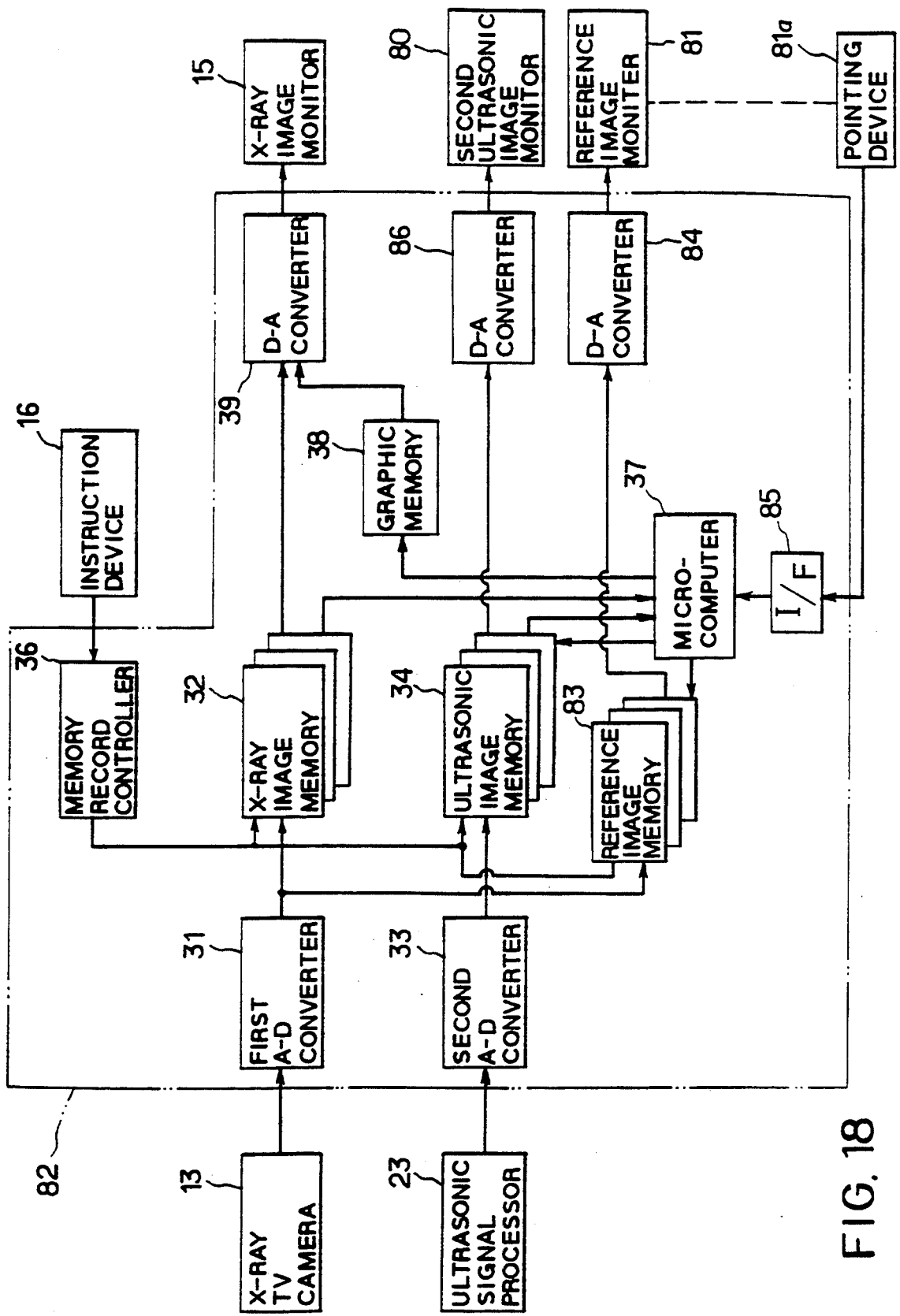
FIG. 18 represents in block form an image processor in the diagnostic apparatus in the fourth embodiment.

The image processor 82 is located in the same manner as in the first embodiment and has a block form as illustrated in FIG. 18. There is provided a reference image memory 83 coupled to the outputs of the A-D converter 31 and the memory record controller 36. The reference image memory 83 is also coupled, by way of a D-A converter 84, to the reference image monitor 81 for displaying reference image data stored therein. The pointing device 81a can send a detected pointing signal to the microcomputer 37 through an interface 85. Moreover, the ultrasonic image memory 34 is also connected to the second ultrasonic image monitor 80 through a D-A converter 86 for displaying the ultrasonic tomographic image after inspection.

Before inspection, a blood vessel being diagnosed is to be fluorographed with contrast medium. The fluorographic image is then be stored in the reference image memory 83 as a reference image of the blood vessel to be inspected.

For diagnosis, the catheter 20 is inserted into the blood vessel under irradiation by X-rays, but without using contrast medium. And then the catheter 20 is pulled back. During the insertion and removal of the catheter 20, for confirmation of the position of the probe 21, the operator can look at the X-ray fluoroscopic image of the monitor 15 and on the X-ray fluoroscopic reference image of the monitor 81 previously imaged at the same diagnostic position, and at the same time, one can observe the ultrasonic tomographic image displayed on the first ultrasonic image monitor 24 for diagnosis.

Then when an interested tomographic image is found on the monitor 24, the operator is to give a record instruction with the instruction device 16. This instruction is possible for one-shot record and continuous record.

In response to the above record instruction, output signals from the ultrasonic signal processor 23 are converted to digital words by the A-D converter 33 and stored into the ultrasonic image memory 34 frame by frame. The microcomputer 37 in the image processor 82 determines the transferred positions of the probe 21 in the same manner as in the first embodiment, and memorizes the positions into one of the work memories therein or in the image memory 34 itself.

Figure 19:
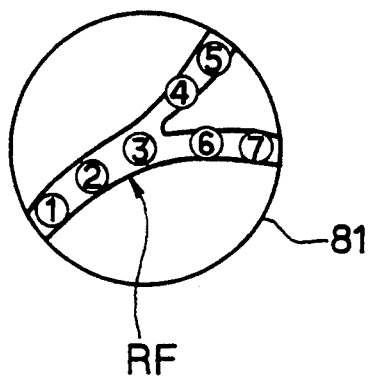
FIG. 19 illustrates an example of a reference image.
Figure 20:
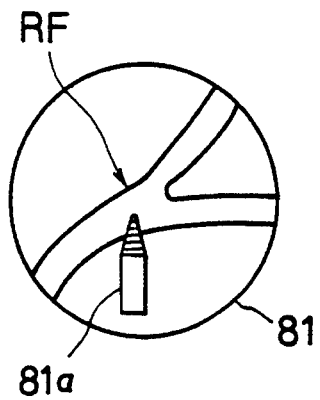
FIG. 20 illustrates a reference image with a pointing device.

After the above diagnosis, it is sometimes necessary to reexamine in detail the ultrasonic tomographic image of the vessel already acquired. In such a case, the microcomputer 37 first outputs a command by which data of the reference image are read out from the reference image memory 83 and transmitted to the reference image monitor 81 through the D-A converter 84. As a result, the reference image RF is displayed on the monitor 81 as shown in FIG. 19 and represents the same vessel as one in tomographic recording. The reference image RF functions as a road-map image of the vessel.

Then, it is an operator's turn to choose a medically desired position on the monitor 81 by using the pointing device 81a (e.g., a light-pen). That is, the desired position is chosen, for example, from the numbered positions shown in FIG. 20 by pointing a specified number (here, the number "three" is chosen).

Figure 21:
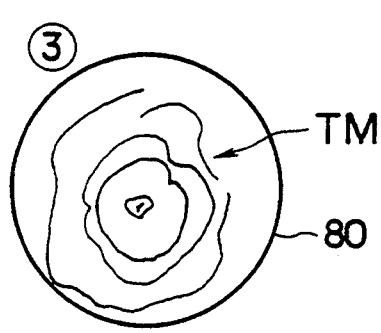
FIG. 21 is an example showing a tomographic image at a single pointed position.

The pointed position signal from the pointing device 81a is to be sent to the microcomputer 37 through the interface 85. In response to the signal, the microcomputer 37 sends a command to the ultrasonic image memory 34 to have it supply frame data corresponding to the pointed position to the second ultrasonic image monitor 80 through the D-A converter 86. By this command, the tomographic image TM crossing transversely across the vessel at the pointed position "three" is displayed, as shown in FIG. 21, on the monitor 80.

Figure 22:
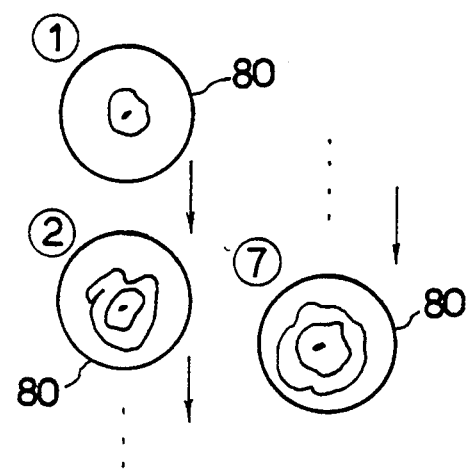
FIG. 22 is an example showing tomographic images at plural pointed positions.

If it is found that the tomographic image corresponding exactly to the pointed position is not stored in the memory 34, a wide variety of substitution measures can be taken. For instance, message saying "not memorized" may be displayed on the monitor 80. As another measure, the nearest position to the pointed one may be determined and the tomographic image at the nearest position may be displayed as a substitute, with making the nearest position blinked on the monitor 81, for instance. For further modification to the pointing, it is possible to designate a continuous curve along the diagnosed vessel so that the positions included in the curve are picked up and the tomographic images at the picked-up positions are displayed like dynamic images on the monitor 80, as shown in FIG. 22 wherein the picked-up positions are "one" to "seven".

Accordingly, the apparatus of this embodiment can provide a convenient way in which ultrasonic tomographic images at interested positions may be selected and displayed readily and accurately, even when the inspection using the ultrasonic probe has been finished. Therefore, widened usage of the diagnostic apparatus is acquired.

In this embodiment, the reference image memory 83 constitutes the X-ray fluoroscopic image storing means. The D-A converter 84 and the reference image monitor 81 make up the X-ray fluoroscopic image displaying means. Further, the pointing device 81a makes up the pointing means. The ultrasonic image memory 34 or the work memory of the microcomputer 37 corresponds to the transferred position storing means. And the processing by the microcomputer 37 corresponds to the tomographic image selecting means. The D-A converter 86 and the second ultrasonic image monitor 80 compose the tomographic image displaying means.

The present invention can also be applied to other vascular systems such as a bile duct, a ureter, and an esophagus.

What we claim is:

1. An apparatus for diagnosing a vascular system of an organism having a lumen in which an inner wall is formed therein, the vascular system including a blood vessel and the organism having a heart, the apparatus comprising:

means for fluorographing the vascular system to be diagnosed by X-rays, said X-rays being transmitted through the organism and converted into electrical image signals;

means for obtaining, in response to a synchronization signal, fluoroscopic two-dimensional image data in accordance with the image signals supplied by the X-ray fluorographing means;

means for probing the vascular system using ultrasonic signals, the ultrasonic probing means having an ultrasonic probe transferrably inserted into the lumen of the vascular system via a catheter incorporating the ultrasonic probe, the ultrasonic probe being able to obtain ultrasonic echoes representing ultrasonic tomographic images of the vascular system, and the ultrasonic echoes being converted into electrical image signals;

means for obtaining, in response to the synchronization signal, tomographic two-dimensional image data in accordance with the image signals supplied by the ultrasonic probing means;

means for determining a structure of the vascular system in accordance with the fluoroscopic two-dimensional image data and the tomographic two-dimensional image data;

means for displaying the structure of the vascular system;

means for monitoring an electrocardiograph signal representing a cardiac cycle of the heart of the organism; and means for selecting a timing sequence having a constant interval in each of the cardiac cycles, wherein each of the fluoroscopic image data obtaining means and the tomographic image data obtaining means comprises means for producing the synchronization signal which is synchronized with said timing sequence while the ultrasonic probe is transferred through the lumen of the vascular system.

2. The apparatus according to claim 1, wherein said structure determining means comprises means for searching transferred positions of the ultrasonic probe transferred through the vascular system for each of the fluoroscopic two-dimensional image data values, means for obtaining section size data of the lumen of the vascular system for each of the tomographic two-dimensional image data values, and means for forming structural data representing the vascular system in accordance with the transferred positions and the section size.

3. The apparatus according to claim 2, wherein said transferred position searching means comprises subtraction means for performing a subtraction pixel-by-pixel between a first fluoroscopic two-dimensional image data value and a subsequent fluoroscopic two-dimensional image data value.

4. The apparatus according to claim 3, wherein said transferred position searching means further comprises a comparison means for comparing subtraction results obtained by the subtraction means with a predetermined threshold level which corresponds to a noise level.

5. The apparatus according to claim 4, wherein said section size data obtaining means comprises an inner wall searching means for searching a position of the inner wall of the vascular system pixel line-by-pixel line for each of the tomographic two-dimensional image data values and a counting means for measuring a section size value of the lumen of the vascular system for each of the tomographic two-dimensional image data values by counting up a total pixel number limited by the inner wall.

6. The apparatus according to claim 3, wherein said structural data forming means comprises a distance calculation means for calculating a transferred distance of the ultrasonic probe transferred through the vascular system in accordance with the transferred positions, a ratio calculating means for calculating a ratio of the section size value between a first tomographic two-dimensional data value and a subsequent tomographic two-dimensional image data value, and a combining means for combining the transferred distance and the ratio into a two-dimensional structural image data value.

7. The apparatus according to claim 3, wherein said section size value is one of a section area and a diameter of the lumen of the vascular system.

8. The apparatus according to claim 7, wherein said combining means comprises means for combining the structural image data in accordance with two axes which are perpendicular to each other, one axis representing the transferred distance in a longitudinal direction of the lumen and the other axis representing the ratio at each position on the transferred position.

9. The apparatus according to claim 8, wherein said structural data forming means further comprises means for calculating a stenosis index of the lumen of the vascular system according to the section size value.

10. The apparatus according to claim 7, wherein said structural data forming means further comprises means for calculating a stenosis index of the lumen of the vascular system according to the section size value.

11. An apparatus for diagnosing a vascular system of an organism having a lumen in which an inner wall is formed therein, the vascular system including a blood vessel, the apparatus comprising:

means for fluorographing the vascular system to be diagnosed by X-rays, said X-rays being transmitted through the organism and converted into electrical image signals;

means for obtaining, in response to a synchronization signal, fluoroscopic two-dimensional image data in accordance with the image signals supplied by the X-ray fluorographing means;

means for probing the vascular system using ultrasonic signals, the ultrasonic probing means having an ultrasonic probe transferrably inserted into the lumen of the vascular system via a catheter incorporating the ultrasonic probe, the ultrasonic probe being able to obtain ultrasonic echoes representing ultrasonic tomographic images of the vascular system, and the ultrasonic echoes being converted to electrical image signals;

means for obtaining, in response to the synchronization signal, tomographic two-dimensional image data in accordance with the image signals supplied by the ultrasonic probing means;

means for determining a structure of the vascular system in accordance with the fluoroscopic two-dimensional image data and the tomographic two-dimensional image data;

first display means for displaying the structure of the vascular system;

first storage means for storing X-ray fluoroscopic image data representing the vascular system, the image data being prepared with contrast medium in accordance with the image signals supplied by the X-ray fluorographing means;

second display means for displaying an X-ray fluoroscopic image as a reference image in accordance with the image data stored in the first storage means;

means for pointing to a desired position along the vascular system shown in the reference image displayed by the second display means;

second storage means for storing transferred positions of the ultrasonic probe, the transferred positions being determined for each sampling period;

means for selecting a tomographic two-dimensional image data value from the tomographic two-dimensional image data values according to the position indicated by the pointing means; and third display means for displaying the tomographic two-dimensional image data selected by the selecting means.

12. The apparatus according to claim 11, wherein said selecting means comprises means for determining the nearest tomographic two-dimensional image data value when the indicated position differs from each of the transferred positions of the ultrasonic probe.

13. The apparatus according to claim 11, wherein said pointing means comprises means for pointing to a single position as the desired position.

14. The apparatus according to claim 11, wherein said pointing means comprises means for pointing to a plurality of positions as the desired position.

15. The apparatus according to claim 11, wherein said pointing means is one of a light-pen, a touch-screen, a mouse, and a keyboard.

16. The apparatus according to claim 11, wherein each of said fluoroscopic image data obtaining means and said tomographic image data obtaining means comprises means for producing the synchronization signal at each predetermined sampling period while the ultrasonic probe is transferred through the lumen of the vascular system.

17. The apparatus according to claim 16, wherein said structural determining means comprises means for searching transferred positions of the ultrasonic probe transferred through the vascular system for each of the fluoroscopic two-dimensional image data values, means for obtaining section size data of the lumen of the vascular system for each of the tomographic two-dimensional image data values, and means for forming structural data of the vascular system in accordance with the transferred positions and the section size.

18. The apparatus according to claim 17, wherein said transferred position searching means comprises substraction means for performing a substraction pixel-by-pixel between a first fluoroscopic two-dimensional image data value and a subsequent fluoroscopic two-dimensional image data value.

19. The apparatus according to claim 18, wherein said transferred position searching means further comprises comparison means for comparing subtraction results obtained by the subtraction means with a predetermined threshold level which corresponds to a noise level.

20. The apparatus according to claim 17, wherein said section size data obtaining means comprises an inner wall searching means for searching a position of the inner wall of the vascular system pixel line-by-pixel line for each of the tomographic two-dimensional image data values and a counting means for measuring a section size value of the lumen of the vascular system for each of the tomographic two-dimensional image data values by counting up a total pixel number limited by the inner wall.

21. The apparatus according to claim 17, wherein said structural data forming means comprises a distance calculation means for calculating a transferred distance of the ultrasonic probe transferred through the vascular system in accordance with the transferred positions, a ratio calculating means for calculating a ratio of the section size value between a first tomographic two-dimensional image data value and a subsequent tomographic two-dimensional image data value, and a combining means for combining the transferred distance and the ratio into a two-dimensional structural image data value.

22. The apparatus according to claim 21, wherein said section size value is one of a section area and a diameter of the lumen of the vascular system.

23. The apparatus according to claim 22, wherein said combining means comprises means for combining the structural image data in accordance with two axes which are perpendicular to each other, one axis representing the transferred distance in a longitudinal direction of the lumen and the other axis representing the ratio at each position on the transferred distance.

24. The apparatus according to claim 21, wherein said structural data forming means further comprises means for calculating a stenosis index of the lumen of the vascular system according to the section size value.

25. An apparatus for diagnosing a vascular system of an organism having a lumen in which an inner wall is formed therein, the vascular system including a blood vessel, the apparatus comprising:

means for fluorographing the vascular system to be diagnosed by X-rays, said X-rays being transmitted through the organism and converted to electrical image signals;

means for obtaining, in response to a synchronization signal, fluoroscopic two-dimensional image data in accordance with the image signals supplied by the X-ray fluorographing means;

means for probing the vascular system using ultrasonic signals, the ultrasonic probing means comprising an ultrasonic probe transferrably inserted into the lumen of the vascular system via a catheter incorporating the ultrasonic probe, the ultrasonic probe being able to obtain ultrasonic echoes representing ultrasonic tomographic images of the vascular system, and the ultrasonic echoes being converted into electrical image signals;

means for obtaining, in response to the synchronization signal, tomographic two-dimensional image data in accordance with the image signals supplied by the ultrasonic probing means;

means for determining a structure of the vascular system in accordance with the fluoroscopic two-dimensional image data and the tomographic two-dimensional image data; and means for displaying the structure of the vascular system.

26. The apparatus according to claim 25, wherein each of said fluoroscopic image data obtaining means and said tomographic image data obtaining means comprises means for producing the synchronization signal for each predetermined sampling period while the ultrasonic probe is transferred through the lumen of the vascular system.

27. The apparatus according to claim 26, wherein each of said fluoroscopic image data obtaining means and said tomographic image data obtaining means comprises memory means including a plurality of frame memories for storing the fluoroscopic and tomographic image data.

28. The apparatus according to claim 26, wherein said structure determining means comprises means for searching transferred positions of the ultrasonic probe transferred through the vascular system for each of the fluoroscopic two-dimensional image data values, means for obtaining section size data of the lumen of the vascular system for each of the plurality of tomographic two-dimensional image data values, and means for forming structural data representing the vascular system in accordance with the transferred positions and the section size.

29. The apparatus according to claim 28, wherein said transferred position searching means comprises subtraction means for performing a subtraction pixel-by-pixel between a first fluoroscopic two-dimensional image data value and a subsequent fluoroscopic two-dimensional image data value.

30. The apparatus according to claim 29, wherein said transferred position searching means further comprises comparison means for comparing subtraction results obtained by the subtraction means with a predetermined threshold value which corresponds to a noise level.

31. The apparatus according to claim 28, wherein said section size data obtaining means comprises an inner wall searching means for searching a position of the inner wall of the vascular system pixel line-by-pixel line for each of the tomographic two-dimensional image data values and a counting means for measuring a section size value of the lumen of the vascular system for each of the tomographic two-dimensional image data values by counting up a total pixel number limited by the inner wall.

32. The apparatus according to claim 31, wherein said structural data forming means comprises a distance calculation means for calculating a transferred distance of the ultrasonic probe transferred through the vascular system in accordance with the transferred positions, a ratio calculating means for calculating a ratio of the section size value between a first tomographic two-dimensional image data value and a subsequent tomographic two-dimensional image data value, and a combining means for combining the transferred distance and the ratio into a two-dimensional structural image data value.

33. The apparatus according to claim 32, wherein said section size value is one of a section area and a diameter of the lumen of the vascular system.

34. An apparatus for diagnosing a vascular system of an organism having a lumen in which an inner wall is formed therein, the vascular system including a blood vessel, the apparatus comprising:

means for fluorographing the vascular system to be diagnosed by X-rays, said X-rays being transmitted through the organism and converted into electrical image signals;

means for obtaining, in response to a synchronization signal, fluoroscopic two-dimensional image data in accordance with the image signals supplied by the X-ray fluorographing means;

means for probing the vascular system using ultrasonic signals, the ultrasonic probing means having an ultrasonic probe transferrably inserted into the lumen of the vascular system via a catheter incorporating the ultrasonic probe, the ultrasonic probe being able to obtain ultrasonic echoes representing ultrasonic tomographic images of the vascular system, and the ultrasonic echoes being converted into electrical image signals;

means for obtaining, in response to the synchronization signal, tomographic two-dimensional image data in accordance with the image signals supplied by the ultrasonic probing means;

means for determining a structure of the vascular system in accordance with the fluoroscopic two-dimensional image data and the tomographic two-dimensional image data;

means for designating a diameter of the ultrasonic probe;

means for calculating an absolute cross-sectional area of the lumen and an absolute diameter of the lumen in accordance with data corresponding to the structure of the vascular system and the diameter of the ultrasonic probe; and means for displaying the structure of the vascular system together with the absolute cross-sectional area of the lumen and the absolute diameter of the lumen.

35. The apparatus according to claim 34, wherein said absolute cross-sectional area and diameter calculating means comprise means for calculating a section area per pixel in accordance with the diameter of the ultrasonic probe and further comprise means for calculating the absolute cross-sectional area of the lumen and the absolute diameter of the lumen using the sectional area per pixel.

36. The apparatus according to claim 35, wherein each of said fluoroscopic image data obtaining means and said tomographic image data obtaining means comprises means for producing the synchronization signal for each predetermined sample period while the ultrasonic probe is transferred through the lumen of the vascular system.

37. The apparatus according to claim 36, wherein said structure determining means comprises means for searching transferred positions of the ultrasonic probe transferred through the vascular system for each of the fluoroscopic two-dimensional image data values, means for obtaining section size data of the lumen of the vascular system for each of the tomographic two-dimensional image data values, and means for forming structural data representing the vascular system in accordance with the transferred positions and the section size.

38. The apparatus according to claim 37, wherein said transferred position searching means comprises subtraction means for performing a subtraction pixel-by-pixel between a first fluoroscopic two-dimensional image data value and a subsequent fluoroscopic two-dimensional image data value.

39. The apparatus according to claim 38, wherein said transferred position searching means further comprises a comparison means for comparing subtraction results obtained by the substraction means with a predetermined threshold level which corresponds to a noise level.

40. The apparatus according to claim 37, wherein said section size data obtaining means comprises an inner wall searching means for searching a position of the inner wall of the vascular system pixel line-by-pixel line for each of the tomographic two-dimensional image data values and a counting means for measuring a section size value of the lumen of the vascular system for each of the tomographic two-dimensional image data values by counting up a total pixel number limited by the inner wall.

41. The apparatus according to claim 37, wherein said structural data forming means comprises a distance calculation means for calculating a transferred distance of the ultrasonic probe transferred through the vascular system in accordance with the transferred positions, a ratio calculating means for calculating a ratio of the section size value between a first tomographic two-dimensional image data value and a subsequent tomographic two-dimensional image data value, and a combining means for combining the transferred distance and the ratio into a two-dimensional structural image data value.

42. The apparatus according to claim 41, wherein said section size value is one of a section area and a diameter of the lumen of the vascular system.

43. The apparatus according to claim 42, wherein said combining means comprises means for combining the structural image data in accordance with two axes perpendicular to each other, one axis representing the transferred distance in a longitudinal direction of the lumen and the other axis representing the ratio at each position on the transferred distance.

44. The apparatus according to claim 41, wherein said structural data forming means further comprises means for calculating a stenosis index of the lumen of the vascular system in accordance with the section size value.

45. The apparatus according to claim 26, wherein said X-ray fluorographing means comprises an X-ray source irradiating the X-rays, an image intensifier converting the X-rays transmitted through the organism to fluorescent lights, and an X-ray TV camera converting the fluorescent lights to the electrical image signals.

46. The apparatus according to claim 32, wherein said combining means comprises means for combining the structural image data in accordance with two axes which are perpendicular to each other, one axis representing the transferred distance in a longitudinal direction of the lumen and the other axis representing the ratio at each position on the transferred distance.

47. The apparatus according to claim 31, wherein said structural data forming means further comprises means for calculating a stenosis index of the lumen of the vascular system in accordance with the section size value.

48. The apparatus according to claim 47, wherein said stenosis calculating means comprises means for determining a maximum value of the section size value as a non-illness portion of the vascular system and a minimum value of the section size value as an illness portion of the vascular system.

49. The apparatus according to claim 48, wherein said stenosis calculating means comprises means for calculating at least one of an index representing the stenosis with respect to a cross-sectional area of the lumen and an index representing the stenosis with respect to a diameter of the lumen.

50. The apparatus according to claim 47, wherein said structure displaying means has a mechanism displaying said stenosis index together with said structural image.

51. The apparatus according to claim 50, wherein said structure displaying means comprises a further mechanism displaying said fluoroscopic image obtained by said fluoroscopic image obtaining means.

* * * * *